(12) United States Patent
Hodson et al.

(10) Patent No.: US 7,080,642 B2
(45) Date of Patent: Jul. 25, 2006

(54) REFILLABLE DEVICE WITH COUNTING MEANS

(75) Inventors: Peter D. Hodson, Trowell (GB); Philip M. Dunn, Surbiton (GB)

(73) Assignee: 3M Innovative Properties Company, St. Paul, MN (US)

( * ) Notice: Subject to any disclaimer, the term of this patent is extended or adjusted under 35 U.S.C. 154(b) by 149 days.

(21) Appl. No.: 10/169,034

(22) PCT Filed: Dec. 19, 2000

(86) PCT No.: PCT/US00/34552

§ 371 (c)(1),
(2), (4) Date: Jan. 3, 2003

(87) PCT Pub. No.: WO01/45768

PCT Pub. Date: Jun. 28, 2001

(65) Prior Publication Data

US 2003/0205227 A1    Nov. 6, 2003

(30) Foreign Application Priority Data

Dec. 22, 1999   (GB) ................. 9930374.5

(51) Int. Cl.
*A61M 11/00* (2006.01)
*A61M 15/00* (2006.01)
(52) U.S. Cl. ............................ 128/200.21; 128/200.11; 128/200.23
(58) Field of Classification Search ........... 128/200.11, 128/200.12, 200.14, 200.21, 200.23, 202.22, 128/203.12, 203.15, 205.23, 205.24, DIG. 1, 128/DIG. 6
See application file for complete search history.

(56) References Cited

U.S. PATENT DOCUMENTS

| 4,950,235 | A | * | 8/1990 | Slate et al. .................... 604/65 |
| 5,192,548 | A | * | 3/1993 | Velasquez et al. |
| 5,564,414 | A | * | 10/1996 | Walker et al. ......... 128/200.23 |
| 5,899,880 | A | * | 5/1999 | Bellhouse et al. |
| 5,925,021 | A | * | 7/1999 | Castellano et al. ......... 604/207 |
| 5,950,016 | A | * | 9/1999 | Tanaka ......................... 396/6 |
| 6,446,627 | B1 | * | 9/2002 | Bowman et al. ........ 128/200.23 |

FOREIGN PATENT DOCUMENTS

| GB | 2263873 | * | 8/1993 |
| WO | WO 90/13327 | * | 11/1990 |
| WO | WO 90/13328 | * | 11/1990 |
| WO | WO 92/08509 | * | 5/1992 |
| WO | WO 92/17231 | * | 10/1992 |

* cited by examiner

*Primary Examiner*—Henry Bennett
*Assistant Examiner*—Dinnatia Doster-Greene
(74) *Attorney, Agent, or Firm*—Ted K. Ringsred (57) ABSTRACT

A refillable medical device comprising a base unit (4) adapted to be engaged with a refill unit (2), the device comprising means for counting the number of different refill units which are engaged with the base unit (4). The device may be in the form of a dry powder or pressurised aerosol inhaler, needleless injector, intravenous drip system etc. The device may comprise means to disable the device after a predetermined number of refill units have been used with the base.

13 Claims, 11 Drawing Sheets

REFILLABLE DEVICE WITH COUNTING MEANS

FIELD OF THE INVENTION

This invention relates to refillable devices of the type comprising a base unit which is engaged with a refill unit and in particular to refillable medical devices having means to count the number of different refill units which have been used with the device.

BACKGROUND TO THE INVENTION

For reasons of economy and in order to reduce the environmental impact of materials usage, there is a growing trend towards the use of refillable devices of various kinds rather than the use of disposable devices. In many cases it is of no great concern how many refill units have been used with a particular device. However, other devices may have a limited life span in the interests of device efficiency, consumer protection, hygiene, manufacturer's liability etc.

U.S. Pat. No. 5,950,016 discloses a recyclable camera and film combination in which the camera comprises means for automatically rewinding the film after the last frame in the film has been shot, means for controlling the lid so as to automatically open when the entire film is rewound into the film cartridge, means for counting the number of film cartridges loaded into the cartridge chamber, and means for making the controlling means inoperative, whereby the lid does not open for the removal of the film cartridge loaded in the cartridge chamber when the counting means reaches a predetermined number of film cartridges and thus prevent the cartridge chamber from receiving any further film cartridges.

U.S. Pat. No. 5,659,837 discloses a developing device in an image forming apparatus having a cartridge loading portion for loading a replaceable toner cartridge, a frame including a hollow portion for receiving a developer supplied from the cartridge. A photosensitive drum installed in the hollow portion and having a surface exposed to the exterior of the frame, and a developer roller installed adjacent to the photosensitive drum, the developing device having a cartridge control device installed on the one side of the cartridge loading portion to control the installation and removal of the toner cartridge in which the cartridge control device includes a cartridge installation and removal device for allowing a user to install or remove the toner cartridge, a counter for counting the number of toner cartridge replacements, and a cartridge removal protector for prohibiting removal of the toner cartridge from the developing device when a predetermined number of toner cartridge replacements is reached so as to prevent contamination resulted from an imbalance between the total amount of the toner supplied and the capacity of a waste toner container.

WO92/17231 discloses a medical inhaler featuring a microelectronic assembly, a receptacle for a container of medication, a triggering element electrically coupled to the microelectronic assembly, positioned inside the receptacle and activated by pressing the container to release a dose of medication. The microelectronic assembly may be a counter, or an interval timer for recording the dosage history of the container, including time intervals between doses. The inhaler includes electrical contact fingers contacting an electrical circuit on the container which stores information about the container in digital form. The digital data storage means includes a set of electrically conductive strips on the container whose spatial pattern represents data about the container and a microelectronic memory. The digital data stored includes the number of doses remaining, the time interval between doses previously actuated, the type of medication, the expiration data, the lot and serial number of the container and other usage information.

In the medical field there are a range of refillable devices, e.g. for the delivery of medicament, saline etc., to a patient which would benefit from a simple, effective system of recording how many refill units have been used with a particular device. It would also be advantageous for the device to be disabled after a predetermined number of refill units have been used.

BRIEF SUMMARY OF THE INVENTION

According to the present invention there is provided a refillable medical device comprising a base unit adapted to be engaged with a refill unit, the device comprising means for counting the number of different refill units which are engaged with the base unit.

The invention provides medical apparatus comprising a base unit having means of counting the number of times fresh refills have been fitted in the base unit. The apparatus does not repeatedly count the same refill unit and therefore the same refill unit may be removed and replaced multiple times e.g. for the purposes of cleaning the base unit, without affecting the count. The base unit may comprise means to visually indicate to the user the count i.e. the number of fresh refills that have been fitted to the base unit. The base unit may comprise means to disable the base unit or prevent engagement of a fresh refill unit after a predetermined number of refills have been used with the base unit. This ensures a base unit is disposed of after its working life or serviced e.g. by replacement of worn components after a predetermined amount of use.

The invention finds particular utility in the medical field in apparatus for delivery of medicament to a patient e.g. dry powder inhalers, pressurised aerosol inhalers, needleless injectors, intravenous line apparatus etc.

The means for counting the number of different refills are of simple mechanical construction which do not require the presence of batteries, motors, microprocessors etc. The counting means need not add significantly to the cost of the device while providing a simple and reliable means of counting the number of refill units used and optionally disabling the device.

DESCRIPTION OF PREFERRED EMBODIMENTS

The means for counting the number of different refills may take a variety of different forms.

According to one embodiment each refill unit comprises a tab which is engaged by the base unit when the refill is fitted thereto. Upon removal of the refill the tab is broken off the refill unit and remains within the base unit as an indication a refill unit has been fitted to the base unit. Thereafter the original refill unit may be engaged and disengaged from the base unit without increasing the "count". When a new (second) refill unit complete with tab is fitted to the base unit the second tab is engaged by the base unit and is retained by the base unit when the second refill unit is removed thus providing an indication that a second refill unit has been used. The base unit may be constructed to prevent engagement of a new refill with tab after a predetermined number of refills have been used with the base unit. For example, the storage space of the base unit for the tabs may have dimensions to accommodate a specific number, say 5, tabs and thereafter engagement of a further tab is prevented since access is prevented by the tabs filling the space.

According to a second embodiment the base unit comprises a counting device comprising a display which may be incrementally moved to display a count e.g. a rotatable wheel, ring or disc. The refill unit comprises an actuator e.g. a projecting finger, which causes incremental movement of the counting device when the refill unit is initially engaged with the base unit and upon first engagement or first removal is permanently deformed or snapped off such that removal and subsequent replacement of the refill unit will not cause further movement of the counting device.

In accordance with one embodiment the device is in the form of a pressurised aerosol inhaler and the refill unit comprises a pressurised aerosol container.

In accordance with a further embodiment the device is in the form of a needleless injector and the refill unit comprises a container of medicament to be injected which may be in liquid or powder form.

In accordance with further embodiments the device is in the form of an intravenous drip system and the refill unit comprises a bag or container of saline, blood etc.

BRIEF DESCRIPTION OF DRAWINGS

The invention will be described with reference to the accompanying drawings in which:

FIG. 15 represents a second fragmentary section through the inhaler of FIG. 13.

DETAILED DESCRIPTION OF THE INVENTION

Figure 1:
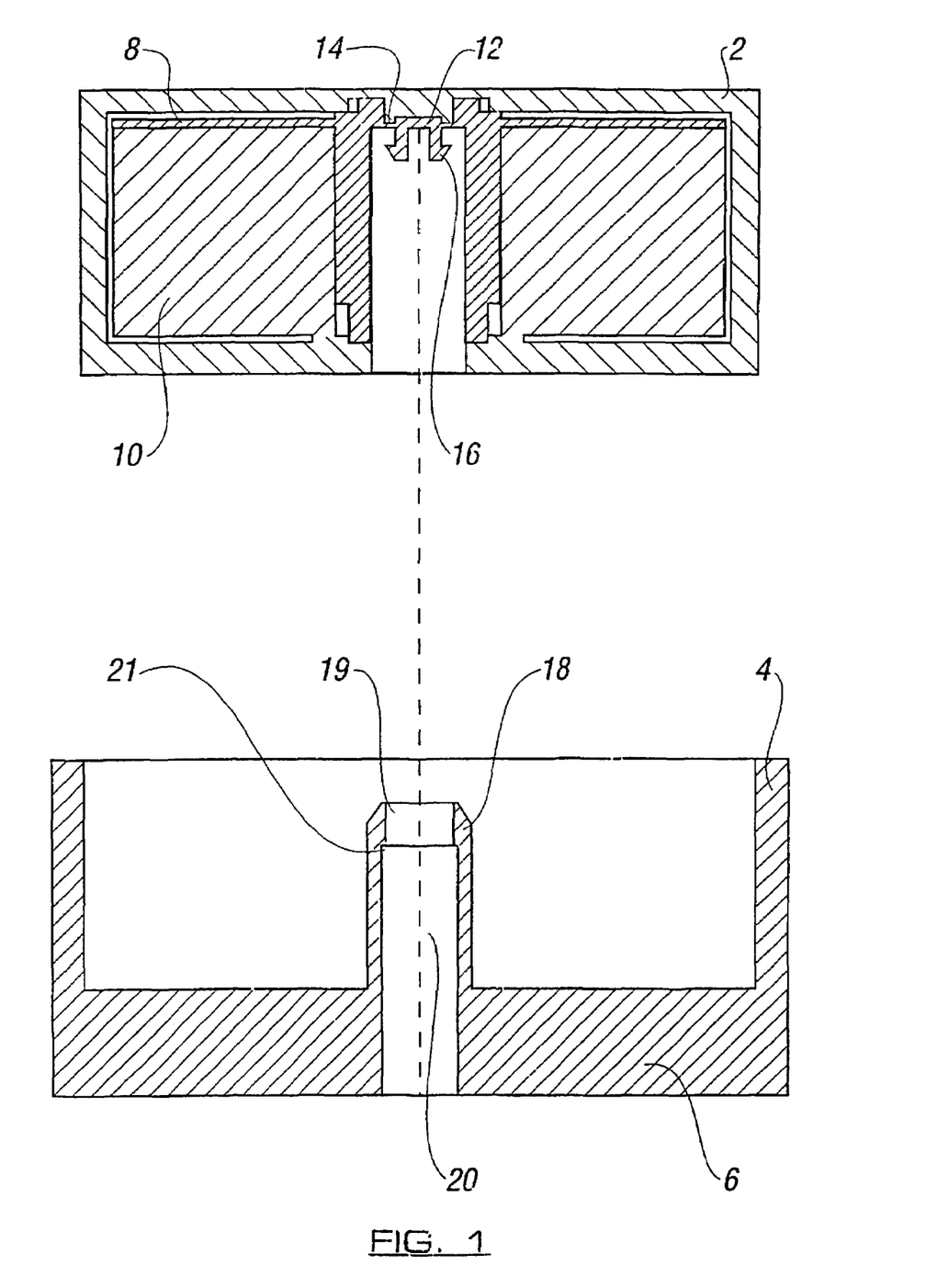
FIG. 1 represents an exploded cross-sectional view through a dry-powder inhaler comprising a base unit and a refill unit.

FIG. 1 shows a replaceable refill unit (2) capable of reversible insertion into a base unit in the form of a reusable inhaler device body (4). The refill unit (2) is in the form of a cassette comprising a flanged spool (8) loaded with medicament-bearing tape (10). Such tapes are disclosed in U.S. Pat. No. 5,192,548. The inhaler body incorporates breath actuated means (not shown) to release the micronised medicament powder from the tape. For example, a triggering release mechanism (not shown) is housed in region (6) of the inhaler device body (4). Full details of such inhalers are disclosed in WO90/13327, WO90/13328 and WO92/08509.

The refill unit (2) and device body (4) shown in FIG. 1 incorporate features of the present invention. The cassette (2) includes a tab portion (12) comprising a plurality of barbed flexible legs (16) and integrally joined to the cassette only by thin finger elements (14). (For convenience, in FIG. 1, the tab (12) is shown moulded as an integral part of the spool (8), although it may be moulded as part of some non-rotating cassette component.) The device body (4) comprises a means for counting (18) in the form of a cylindrical storage chamber (20) having a frustoconical inlet (19) which has a diameter slightly smaller than that of the chamber (20) to create an annular retaining ledge (21).

Figure 2:
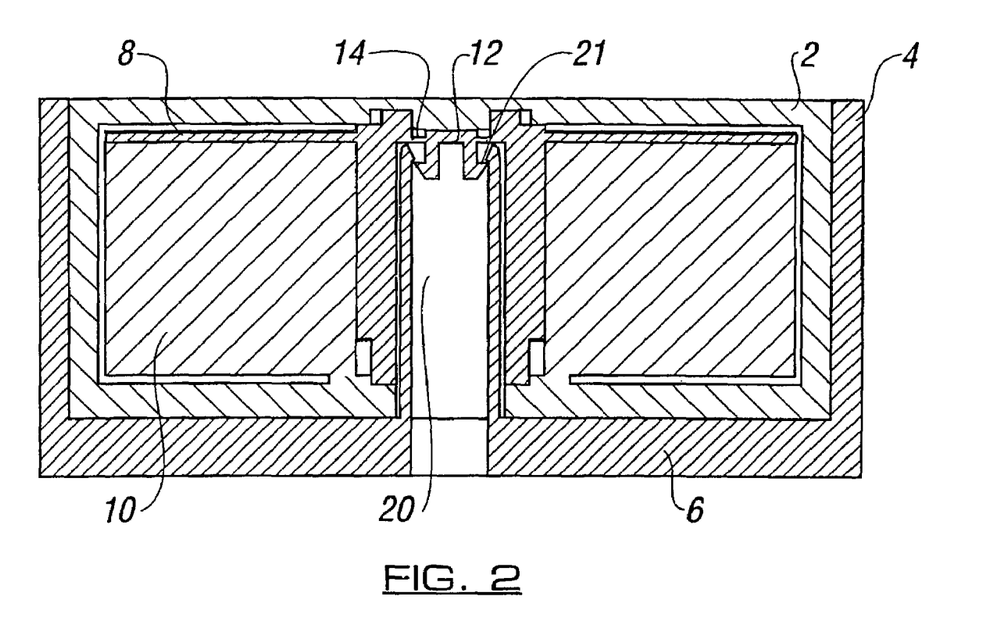
FIG. 2 represents a cross-sectional view of the assembled dry-powder inhaler of FIG. 1.
Figure 3:
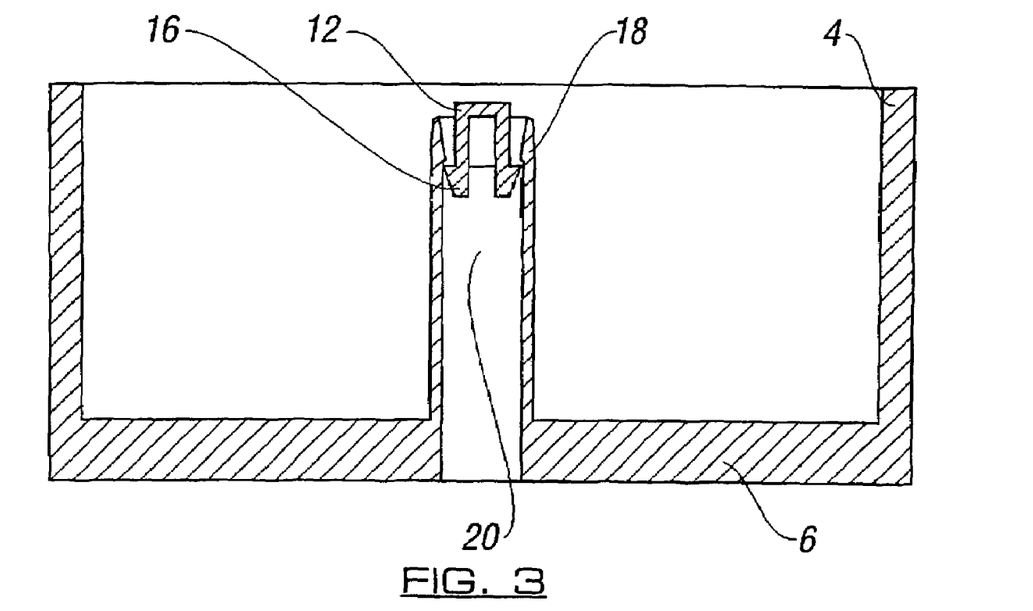
FIG. 3 represents a cross-sectional view of the base unit of the inhaler of FIGS. 1 and 2 with a tab from the refill unit of FIG. 1 in it.

In use the patient inserts a replaceable cassette (2) into the inhaler device body (4), causing the detachable tab (12) to enter the storage chamber (20), with its flexible legs (16) biased inwards by the inlet (19), and then released to spring outwards once the inhaler has been assembled (FIG. 2).

Figure 4:
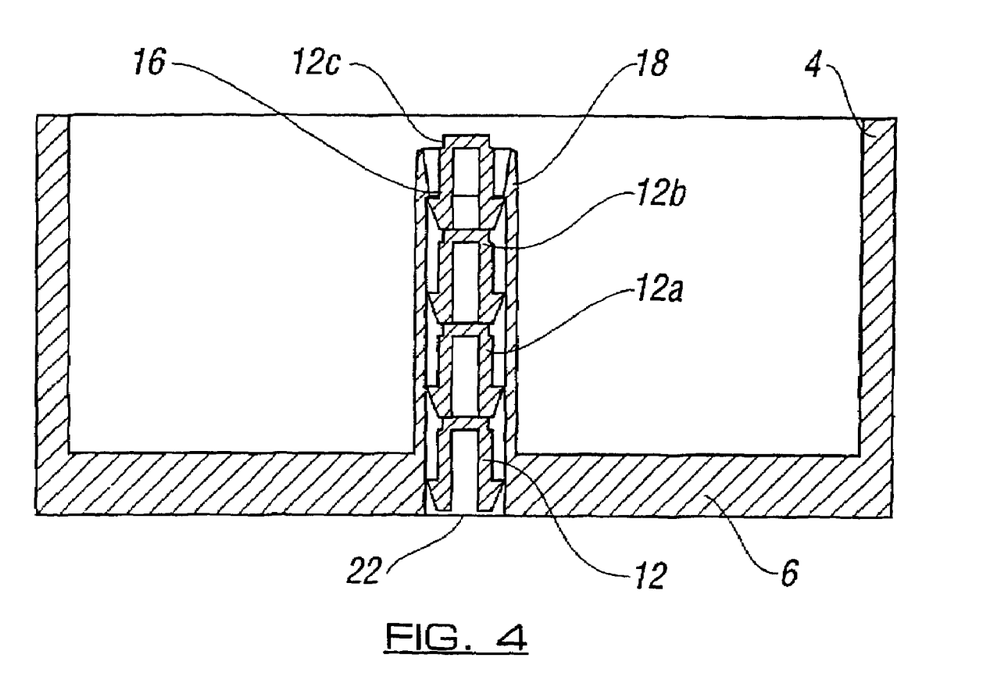
FIG. 4 represents a cross-sectional view of the base unit of the inhaler of FIGS. 1 and 2.

For each subsequent new cassette refill inserted, a further detachable tab (12a, 12b, 12c, etc.) will be deposited into the chamber (20) in the device body (4). FIG. 4 shows the device body after four fresh refills have been inserted and removed in turn. At this point, the patient is warned not to use the device body further by the appearance of a tab (12) near opening (22). This prevents the patient from tending to use the reusable device body with more refills than its intended life. This is important for pharmaceutical devices, such as inhalers, where over-use of an inhaler might result in enough wear and tear to prevent it dispensing accurate and safe doses.

In one embodiment (not shown) a transparent window is secured over opening (22), preventing insertion of further refills after insertion of the intended number of refills. Generally in pharmaceutical devices, however, it is desirable to allow the continued refilling of the device body, in order to provide contingency for emergencies when the patient has not appreciated they have reached the intended refill number limit. In this case, any additional cassettes inserted will result in earlier tabs being expelled from the device through the opening (22). The visible (and possibly tactile, for vision impaired patients) presence of a tab near the opening (22) will continue to remind the patient to obtain a new device body (4), however.

An additional feature of the invention is that provision could be made to store X+1 tabs in the storage space (20), where X is the intended maximum number of refill units. In this case, the patient would be able to see the tabs accumulating in the storage space (20), and a warning line would show them when X cassettes had been inserted. One purpose of the X+1th space would be to give the manufacturer warning that the device body (4) had been used beyond its guaranteed life, for product liability reasons.

It will be appreciated that the detachable tabs (12) are well protected from tampering inside the cassette (2). As an additional security feature, for example to prevent malicious product liability disputes or claims, the internal surfaces of the chamber (20) could be moulded smooth to allow microscope examination for scratches caused by tabs that have entered the chamber (20) but have subsequently been pushed out through opening (22) by a tampering patient.

Figure 5:
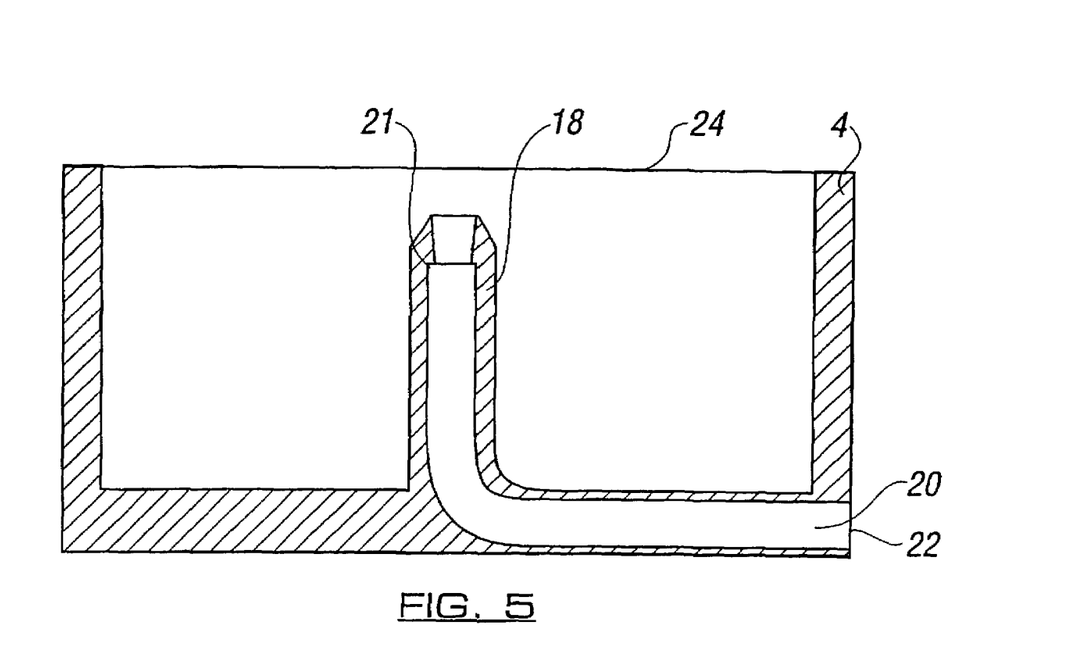
FIG. 5 represents a cross-sectional view of an alternative base unit of a dry-powder inhaler.

FIG. 5 shows schematically a device body (4) comprising a means for counting comprising a storage chamber (20) for tabs. This chamber (20) is in the form of a quadrant arc and a straight portion and serves the purpose of holding a considerably greater number of detachable tabs than the embodiment shown in is FIGS. 1 to 4. Alternatively, the tube could be in the form of a semi-circular arc (not shown) to cause the tabs to reach the top surface (24) of the device body when the device has reached its design life, thus providing a more forceable reminder to the patient that a new device body should be obtained.

Figure 6:
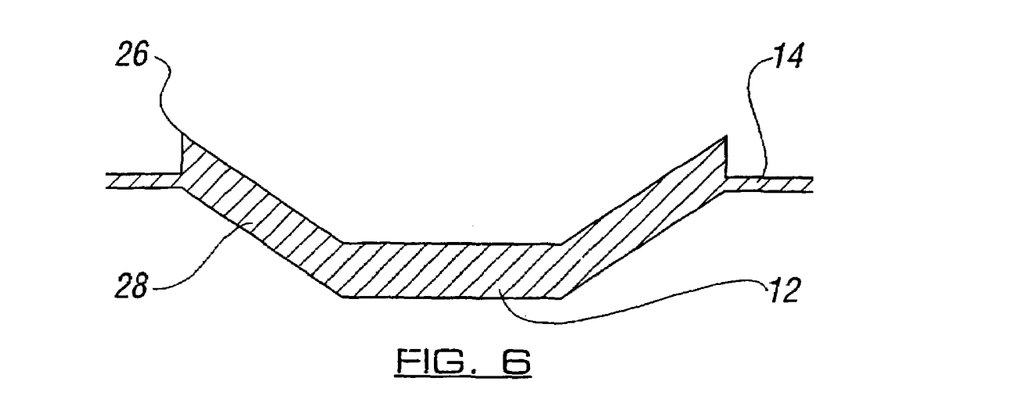
FIG. 6 represents a fragmentary cross-section through an alternative form of tab to that shown in the refill unit in FIGS. 1 and 2.

FIG. 6 shows schematically (at higher scale) an alternative detachable tab portion (12) suitable for use in the present invention, comprising an open cup with sloping walls (28) of sufficient flexibility to act in a manner analogous to that of the flexible legs (16) in FIG. 1. The rim (26) of said walls, which may not be continuous around 360°, is arranged to interface with the circular retaining ledge (21), to prevent the tab (12) being removed from the storage chamber (20) upon refill removal, but instead to cause the thin finger portions (14) attached to the refill (2) to tear. The advantage of such a tab geometry is that the tabs can stack much closer together, inside one another, allowing more tabs to be stored in a given device body thickness.

Figure 7:
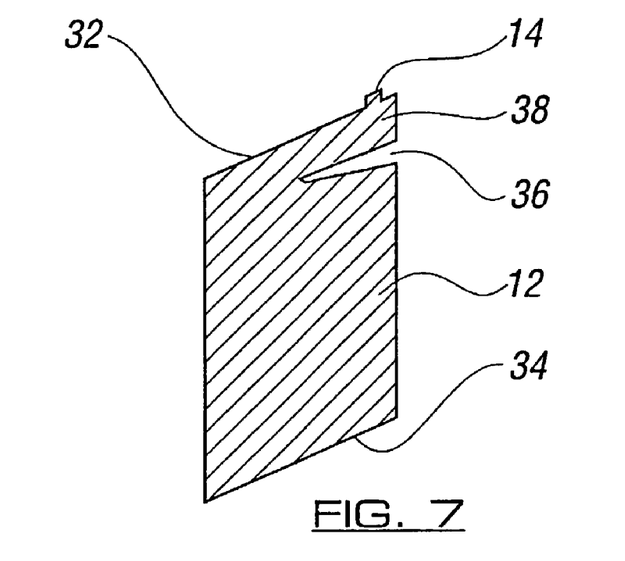
FIG. 7 represents a cross-section through a tab suitable for use on a refill unit for use in the invention.
Figure 8:
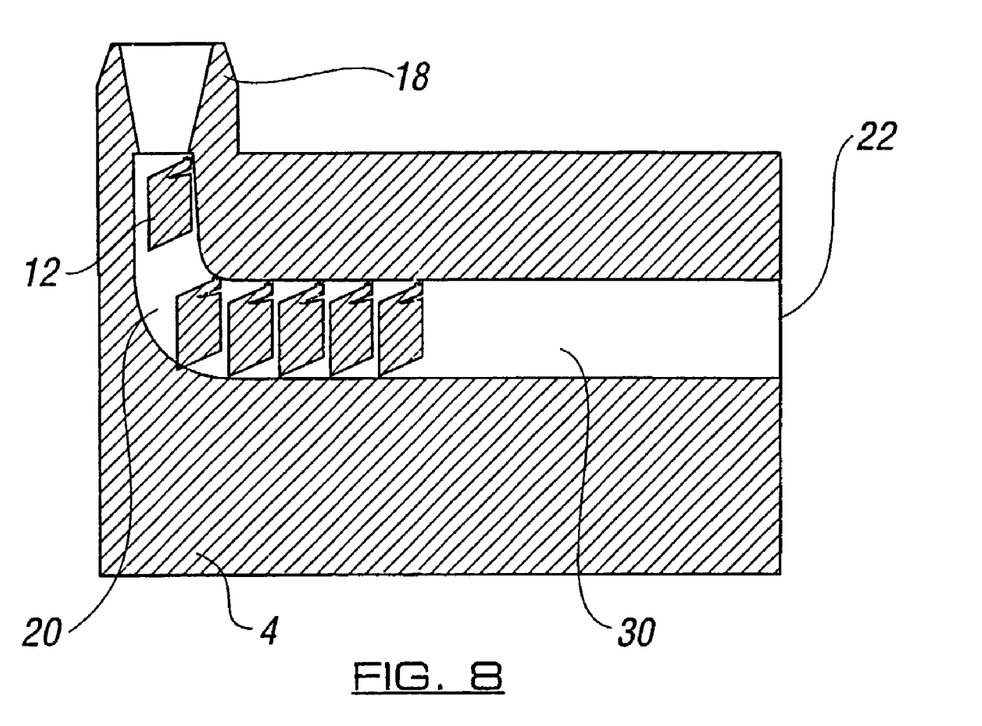
FIG. 8 represents a cross-section through a base unit containing tabs as shown in FIG. 7.

An alternative embodiment of the invention is shown schematically in FIGS. 7 and 8. This embodiment is also suitable for storing a large number of tabs in a small device body thickness. The tabs (12) are in the form of wedges, having angled surfaces (32, 34) and a notch (36). A thin integral flexible finger (14) attaches the tab (12) to the refill cassette (not shown).

The device body (4) (shown in part) comprises a tab storage chamber (20) with a straight portion (30) in which many tabs can be held. The angled surfaces (32, 34) serve to allow each subsequent tab to push its predecessors sideways along the straight portion of tube (30). The hinged top (38) of each tab is pushed down slightly by the tube roof, causing the notch (36) to close-up slightly and thereby allowing the tabs to be held in place in the tube. Alternatively, small projections (not shown) at the tube opening (22) could be provided to prevent tabs being shaken out of the device body, whilst allowing them to be pushed out by further tabs in an emergency.

As an alternative (not shown), the opening (22) of FIG. 8 might be closed off, and the tabs not provided with hinged tops (38), in order that there is no possibility of stress relaxation causing the hinged tops to loosen in the tube (30).

The tabs (12) could be coded to enable the manufacturer, user, patient or doctor etc., to know what variants or batch numbers of refill units had been used in a device body.

FIGS. 9 to 12 illustrate the application of the present invention to a breath actuated pressurised aerosol inhaler. Full details of the inhaler are not shown but are disclosed, for example in GB2263873 the disclosure of which is incorporated herein by reference. Examples of such inhalers are commercially available under the registered trade mark EASI-BREATHE from Baker Norton.

Figure 9:
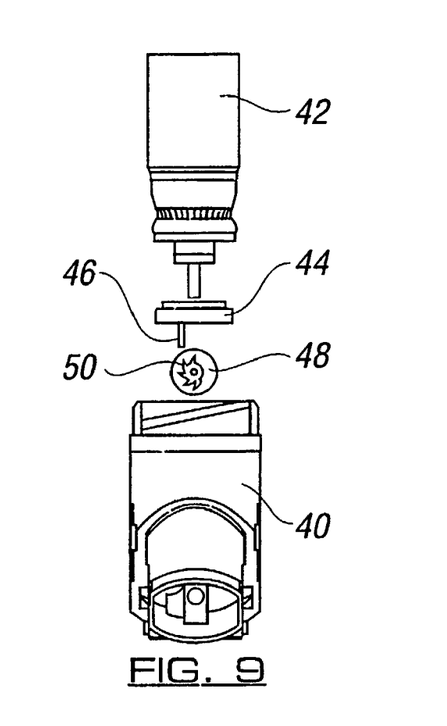
FIG. 9 represents an exploded view of a pressured aerosol inhaler comprising a base unit and a refill unit, FIG. 10 represent a view of the inside of the inhaler of FIG. 9.

The inhaler comprises a base unit which comprises a housing incorporating a mouthpiece and breath actuation mechanism. Part of the housing is shown at (40). A refill unit is in the form of a pressurised aerosol container (42) having secured thereto in the region of the valve ferrule a ring component 44 having a downwardly projecting finger 46.

The base unit (40) is provided with a counter 48 in the form of a rotating disc. The disc may be viewed through a window (not shown) in the back of the inhaler housing and the disc contains appropriate marking to signify the number of counts. The back of the disc comprises a toothed wheel (50).

Figure 10:
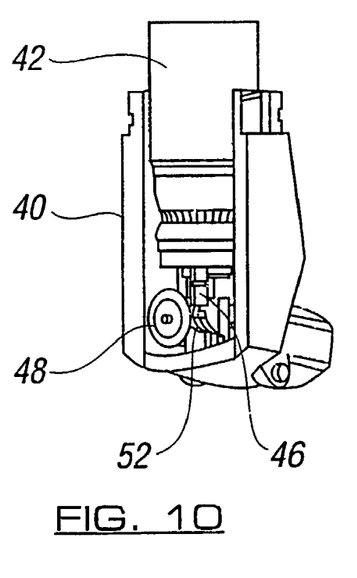
Figures 11, 12:
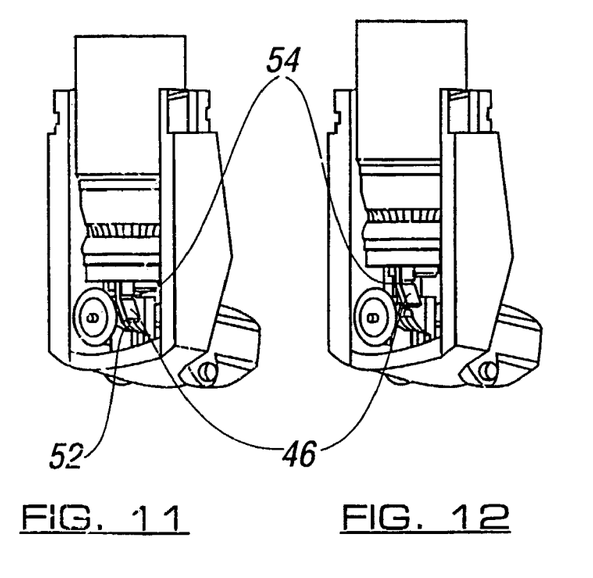
FIG. 11 represents a view of the inside of the inhaler of FIG. 9 after insertion of a refill unit.
FIG. 12 represents a view of the inside of the inhaler of FIG. 9 prior to removal of the refill unit.

When the refill unit is inserted in the base unit the downwardly projecting finger (46) engages a tooth on the toothed wheel (50) causing the wheel and disc to rotate by one increment (FIG. 10). As insertion of the refill unit is completed the finger (46) engages the curved surface (52) in the base unit causing the finger (46) to be permanently deformed (FIG. 11). This deformation is aided by a notch (54) part way along the finger (46). Thereafter the refill unit may be repeatedly removed and inserted in the base unit without incrementing the counter since the deformed finger is no longer able to engage the toothed wheel. In an alternative embodiment (not shown), insertion or removal of the refill unit might cause the finger to break off.

The counter can be designed to allow a set number of aerosol refills to be used by varying the number of teeth. After the set number of aerosol refills have been inserted it may either show a visual warning that a new device is now required, possibly through a window in the device, or it may have a mechanism that would prevent any further aerosol refills being added, or both.

The ring component (44) attached to the ferrule may have a locating feature to ensure the finger will always line up with the counter. It may also be covered with a shrouding component to protect the finger before the aerosol refill is fitted to the device. An interlocking system may be incorporated to prevent the shrouding component from exposing the finger unless it is fitted into the inhaler.

Figure 13:
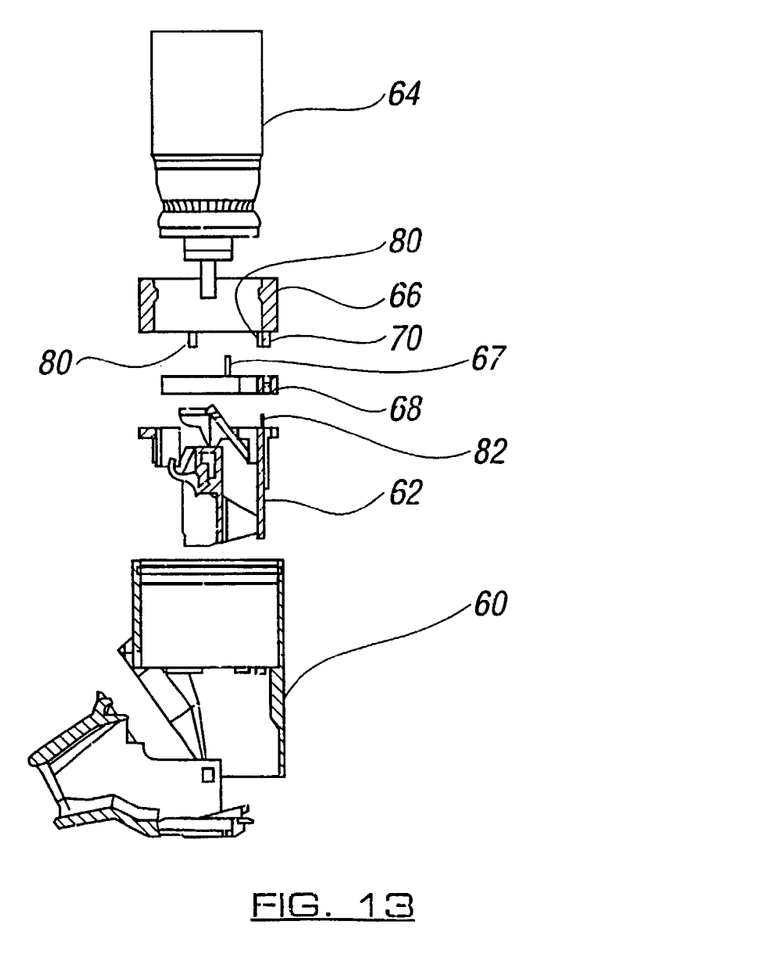
FIG. 13 represents an exploded view of a pressurised aerosol inhaler comprising a base unit and refill unit.
Figures 14, 15A, 15B:
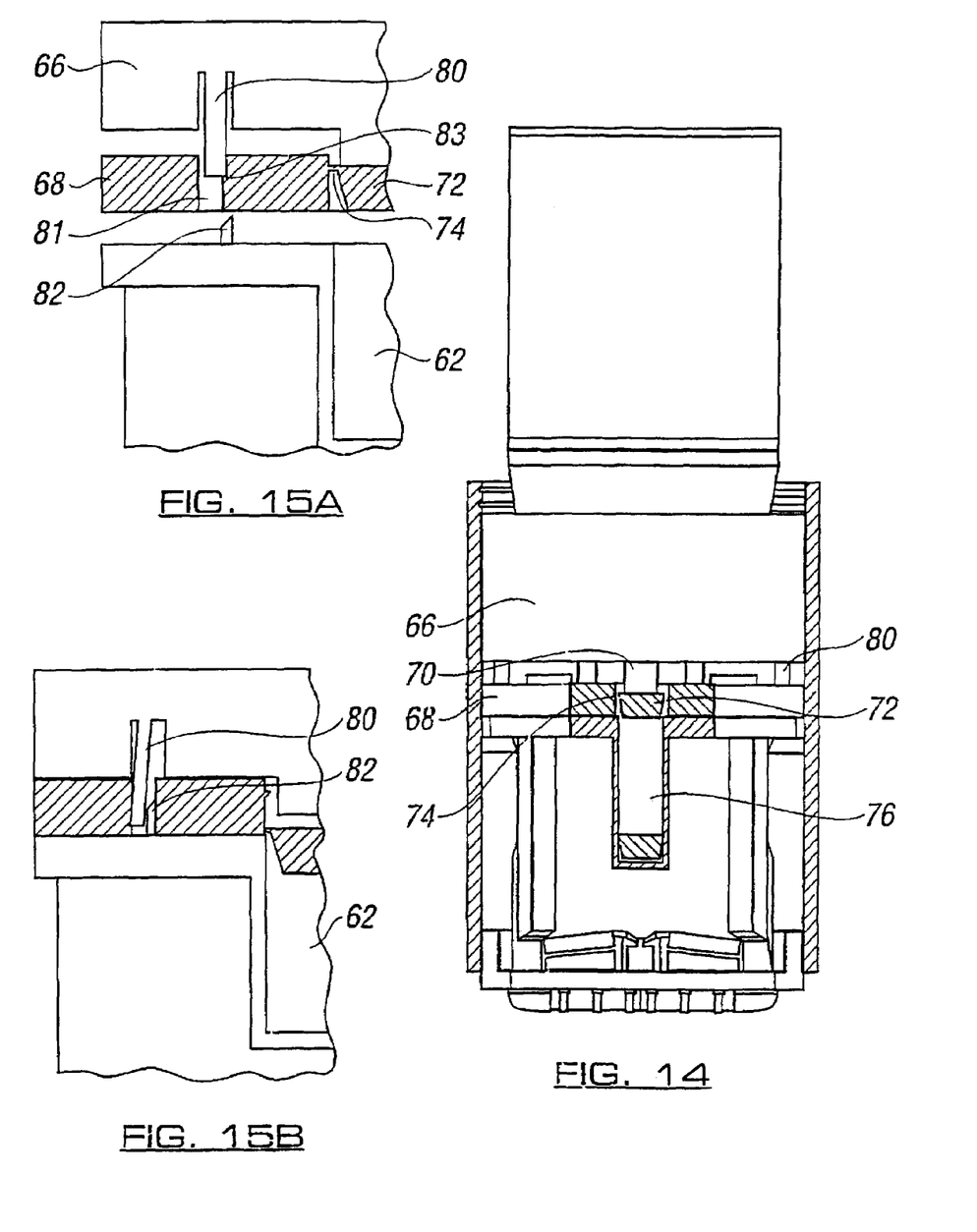
FIG. 14 represents a first fragmentary section through the inhaler of FIG. 13 showing the arrangement of the tab.

FIGS. 13 to 15 illustrate the application of the invention to a different breath actuated pressurised aerosol inhaler. Full details of the inhaler are disclosed in EP 147028 the disclosure of which is incorporated herein by reference. Examples of such inhalers are commercially available under the registered trade mark AUTOHALER from 3M United Kingdom plc.

The inhaler includes a base unit comprising a housing (60) defining a mouthpiece and a nozzle block and triggering mechanism (62). The refill unit comprises aerosol container (64) and upper and lower ring components (66, 68). The upper ring component (66) is secured to the aerosol container (64) and comprises a finger (70). The lower ring component (68) comprises a tab (72) held by thin web elements (74).

The lower ring component (68) is held captive to the upper ring component (66) with a number of barbed features (67) which prevent the two components from coming apart but will allow them to come closer together when the refill unit is fitted to the base unit. When the refill unit is fitted to the base unit, and the aerosol is actuated in the device for the first time, the upper and lower components come together causing the finger (70) on the upper component to break the tab (72) off the lower ring component and push it into a channel (76) formed on the back of the nozzle block of the base unit. The tab (72) is prevented from falling out of the channel (76) by a slight interference fit. Following insertion of the refill unit and the breaking of the tab, the aerosol and upper component will be free to move up and down during normal actuation of the device. The refill unit may be removed and replaced.

New refill units can be inserted into the base unit and tabs broken off until the channel (76) is full, actuation of subsequent further refill units being prevented by the presence of the final, additional captive tab.

Additional features may be incorporated to prevent the upper and lower ring components coming together until they are assembled in the base unit, thus preventing the tab (72) from being prematurely broken off and not captured in the channel of the base unit which would defeat the function of the system of the invention. FIGS. 15(a) and (b) illustrate such an arrangement. Upper ring component comprises a pin (80) which is partially accommodated in a recess (81) in the lower ring component (68) prior to assembly with the base unit. The pin (80) is prevented from fully entering the recess (81) by engagement with ledge (83) (FIG. 15(a)). The nozzle block (62) of the base unit comprises a guide finger (82) and when the upper and lower ring components are engaged with the base unit the guide finger (82) deflects pin (80) away from ledge (83) allowing pin (80) to fully enter recess (81). Tab (72) is broken off as the upper and lower ring components come fully together as they are assembled with the base unit (FIG. 15(b)).

In an alternative embodiment the base unit could start with a supply of tabs, which would then be removed, one by one, by insertion of refill units. A refill unit is configured so that it could not be used successfully unless a tab is present: for example, the tab from the base unit might be necessary to hold the refill in place, or to allow it to operate (e.g. mechanically). The individual refill units are only capable of a single insertion. The base unit is limited in its number of reuses. It is necessary to ensure that old tabs could not be used to "resupply" the base unit for unauthorised further use.

Figure 16:
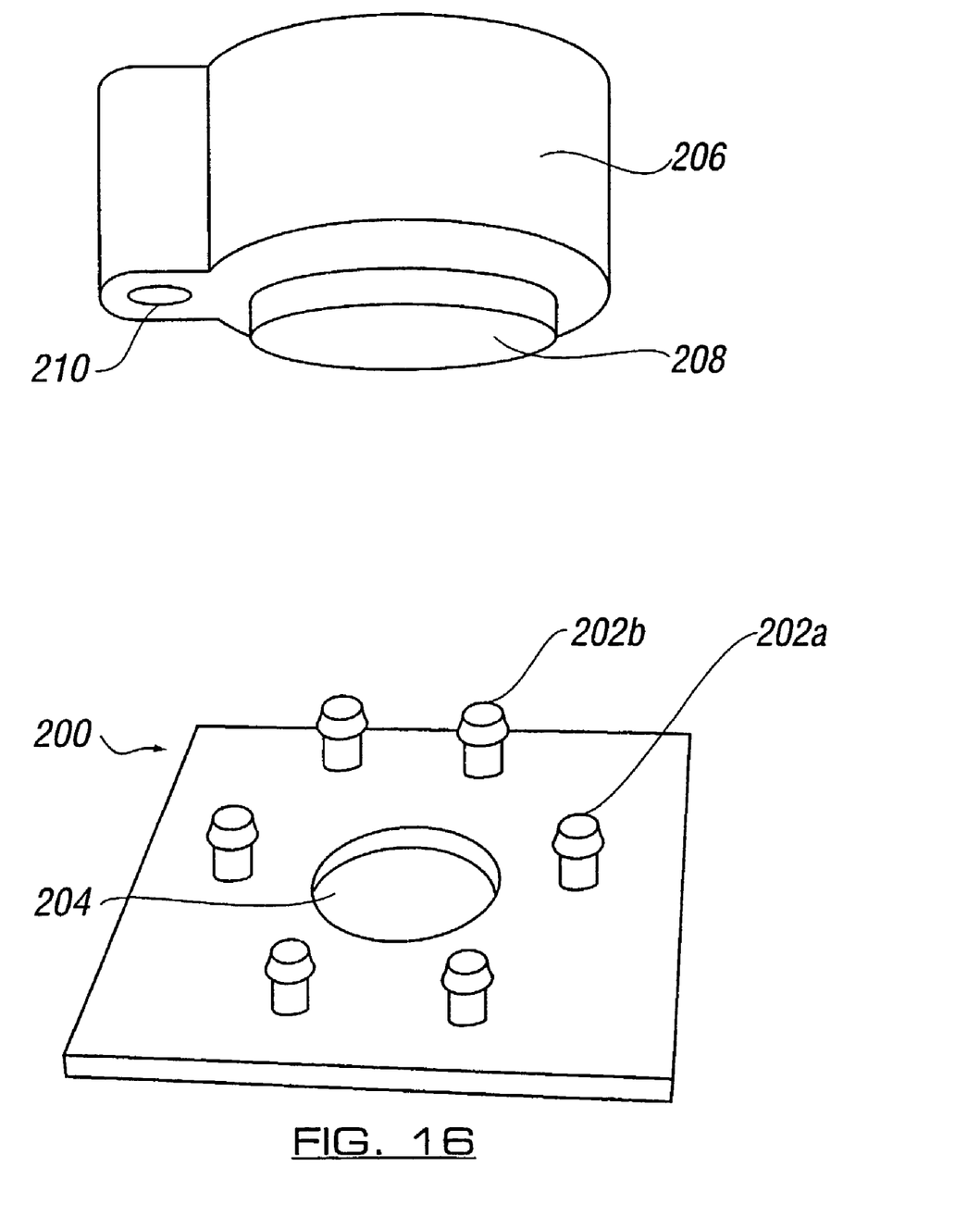
FIG. 16 represents an exploded view of a further inhaler in accordance with the invention.

FIG. 16 shows an example of such an embodiment which comprises a base unit (200) with a supply of six integrally moulded plastic tabs (202a etc.) and with a recess (204) for aligning a refill unit in place. A refill unit (206) for use with this base unit has a corresponding raised area (208) to align with recess (204). An aperture (210) in the refill unit, with an overhanging lip edge (not shown) serves to align with one of the tabs (202a).

In use, the user fits the refill unit (206) into the base unit (200), in such a way that the raised area (208) aligns with the recess (204) and one of the tabs (202a) aligns with the hole (210). The tab (202a) serves to locate and secure the refill unit (206) in the base unit (200) in such a way that it can be successfully used. When the refill unit (206) is subsequently removed, the lip (not shown) of the hole (210) causes the captive tab (202a) to fracture from the base unit (200) at its proximal end. That tab (202a) thus remains in the refill unit (206) and is protected from easy removal by the user, thus preventing re-use of the spent refill unit (206). The unit (200) meanwhile has "counted" one refill unit and now only has five remaining tabs (202b etc.) for further use. The user must then align the base unit (200) with the next refill unit such that the latter's hole aligns with one of the five remaining tabs (202b etc.).

In an alternative embodiment (not shown), the base unit comprises a spring loaded supply of stacked tabs to advance tabs sequentially. The refill unit is configured to engage with (and subsequently remove) the outermost tab of the stack only.

Figure 17:
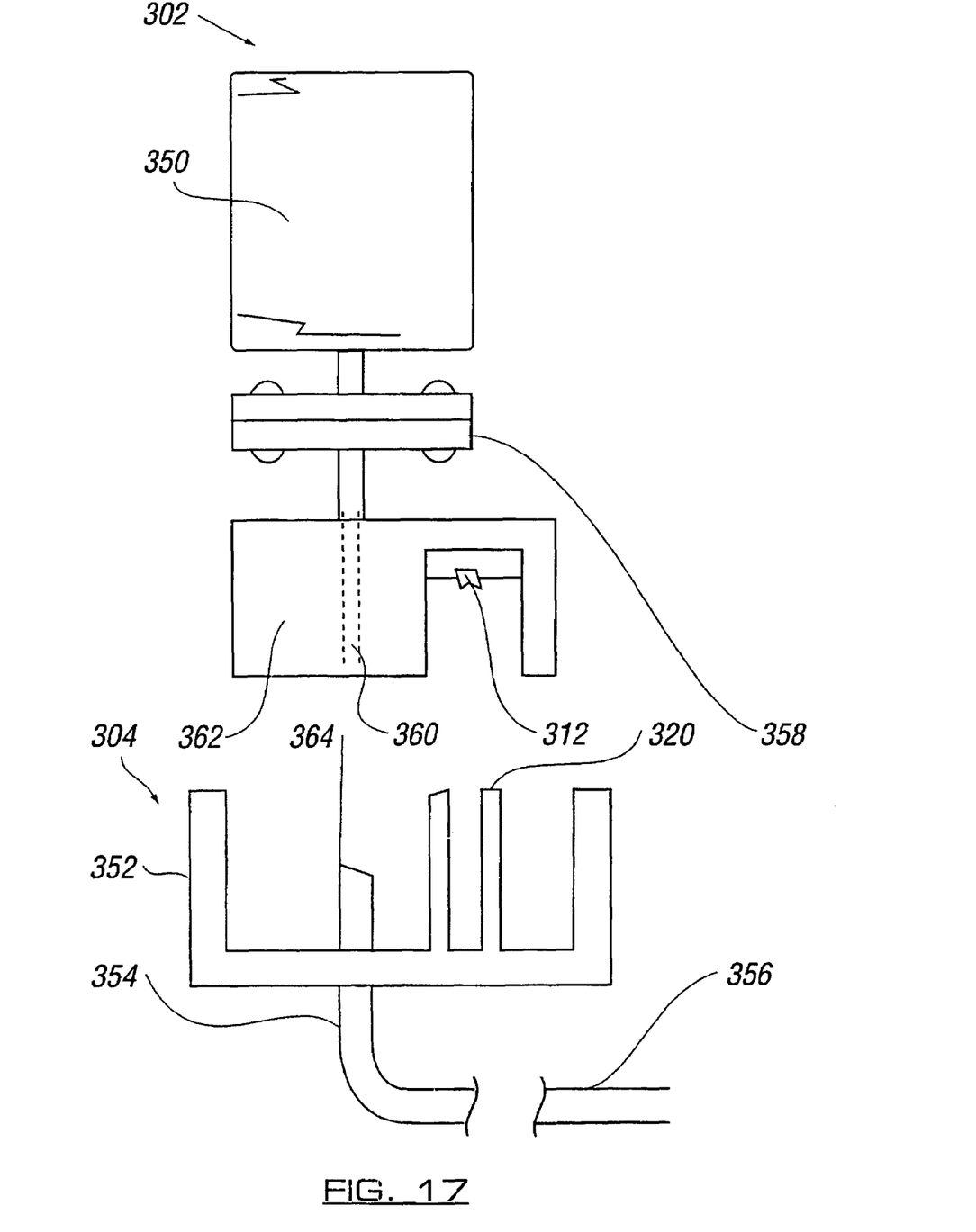
FIG. 17 is a schematic diagram of an intra-venous drip system in accordance with the invention and FIG. 18 is a schematic diagram of part of a needleless injector in accordance with the invention.

FIG. 17 shows schematically a replaceable refill unit (302) comprising a flexible bag (350) containing blood, saline etc. and capable of reversible insertion into a base unit (304) in the form of a connector plate (352) fitted to a tubing line (354) connected to an intravenous needle (356) inserted in a patient's arm (not shown). Similar systems, but without the counting means of the present invention, are disclosed in U.S. Pat. No. 5,947,937 the disclosure of which is incorporated herein by reference. For example the refill unit may have configurations and fittings (358, 362) which provide coding for the blood group in the flexible bag (350). The connector plate (352) would have a geometry and/or fittings of a shape coding for the recipient patient's blood group, such that only refill units (302) containing the same blood group would be capable of insertion into the connector plate (352).

The refill unit (302) and base unit (304) shown in FIG. 17 incorporate features of the present invention. The refill unit includes a tab portion (312) of similar form and mounting as tab portion 12 of FIG. 1. The base unit (304) comprises a cylindrical storage chamber (320) having an inlet geometry of the type possessed by the storage chamber (20) of FIG. 1.

In use, a blood containing replaceable refill unit (302) is inserted into the base unit (304), causing the end (364) of the tubing line (354) to mate with the inside bore (360) of the refill unit's connector fittings (362), thereby allowing blood from the flexible bag (350) to pass via the tubing (354) and the hypodermic needle (356) into the patient's arm (not shown). Insertion of the refill unit (302) into the base unit (304) also causes the detachable tab (312) to enter the storage chamber (320) and to be left there upon removal of the refill unit (302). In this way, a record is left in the base unit (304) connected to the patient of how many refill units of blood have been supplied to the patient. It is clearly of importance to know this information, and this invention provides automatic means of recording the number of blood bags supplied.

Figure 18:
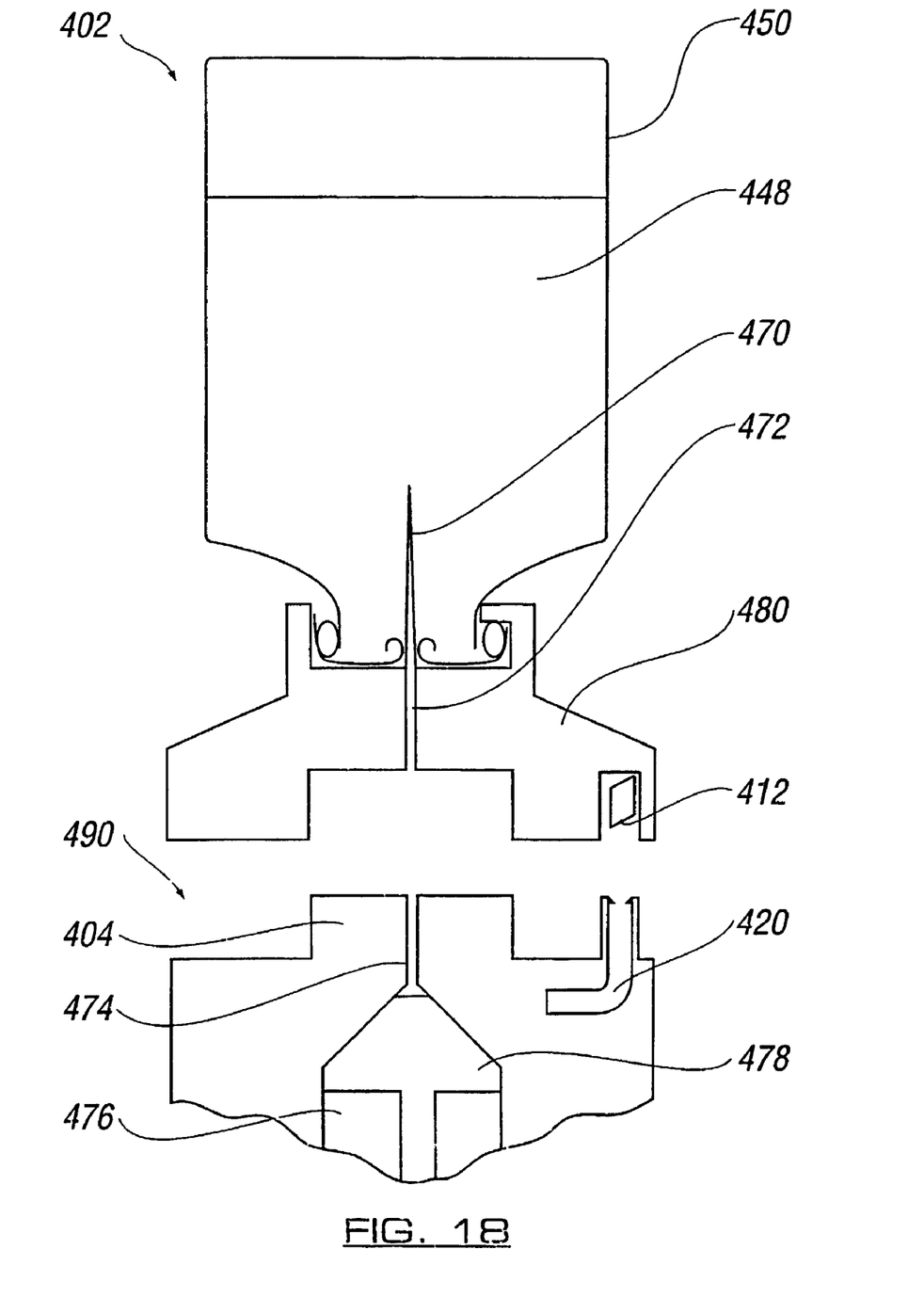

FIG. 18 shows schematically a replaceable refill unit (402) comprising a medicament vial (450) containing a liquid medicament formulation (448) to be administered to the skin. The replaceable refill unit (402) also comprises a plastic connector (480) capable of reversible engagement with a needleless jet injector system (shown partially at 490) in the form of a base unit (404). When the vial (450) and connector (480) are assembled together, a narrow exit passageway from the vial (450) is formed via a vial-piercing needle (470) and an internal tube (472), The injector system (490) comprises a spring-driven piston (478) in a cylinder (476), use of which piston arrangement, after the refill unit (402) has been disengaged, allows administration of a dose of medicament in the form of a high velocity liquid jet from the cylinder (476) via the nozzle (474) into the patient's skin (not shown).

Similar refill systems for needleless jet injector systems, but without the counting means of the present invention, are disclosed in U.S. Pat. Nos. 4,507,113 and 4,883,483 the disclosure of which is incorporated herein by reference.

The refill unit (402) and base unit (404) shown in FIG. 18 incorporate features of the present invention. The refill unit includes a tab portion (412) of similar form and mounting as tab portion 12 in FIG. 8. The base unit (404) comprises a storage chamber (420) of a similar type to that shown in FIG. 8.

In use, a replaceable refill unit (402) is engaged with the needleless jet injector base unit (404), thereby allowing medicament formulation from the vial (450) of the refill unit (402) to be drawn into the cylinder (476) of the jet injector (490). Insertion of the refill unit (402) into the base unit (404) also causes the detachable tab (412) to enter the storage chamber (420) and to be left there upon removal of the refill unit (402). In this way, a record is left in the needleless injector's base unit (404) of how many refill units have been used with the jet injector (490). This information may be important for providing a record of the medicament administered to an individual patient, and may also be of importance for monitoring use of a particular jet injector where uncontrolled re-use before disposal is undesirable.

It will be appreciated that other arrangements of the present invention, including ones compatible with a bayonet or screw engagement action, are possible. It will also be apparent that the present invention is also suited to other applications, such as use in refillable dry powder needleless injection systems such as that disclosed in U.S. Pat. No. 5,899,880 the disclosure of which is incorporated herein by reference.

The invention claimed is:

1. A refillable medical device comprising a base unit adapted to be engaged with a refill unit, wherein the device includes medicament and a counter that indicates the number of fresh refill units that have been engaged with the base unit without repeatedly counting the same refill unit, and after a predetermined number of fresh refills have been used with the base unit, the base unit becomes disabled or engagement of a fresh refill unit is prevented.

2. A refillable medical device as claimed in claim 1, wherein the counter includes a chamber adapted to receive a tab attached to the refill unit so as to engage and detach the tab from the refill unit.

3. A refillable medical device as claimed in claim 2, wherein the chamber is dimensioned to accommodate a predetermined number of tabs whereupon engagement of a fresh refill unit with the base unit is prevented.

4. A refillable medical device as claimed in claim 2, wherein the base unit is constructed so that tabs present in the chamber are visible.

5. A refillable medical device as claimed in claim 1 wherein the base unit includes a display that indicates the number of fresh refill units that have been engaged with the base unit, the display incrementally advancing upon engagement of a fresh refill unit.

6. A refillable medical device as claimed in claim 5 in which the display is in the form of a rotatable disc.

7. A refillable medical device as claimed in claim 6 in which the rotatable disc is associated with a toothed wheel that is engaged by a finger attached to a refill unit to incrementally move the disc, and the base unit adapted to deform or break said finger to prevent subsequent engagement of the finger with the toothed wheel.

8. A refillable medical device as claimed in claim 2 in which the tab is detached from the refill unit when the refill unit is detached from the base unit.

9. A refillable medical device as claimed in claim 1, wherein the device is a dry powder inhaler and the refill unit is in the form of a cassette bearing powdered medicament.

10. A refillable medical device as claimed in claim 1, wherein the device is a pressurized aerosol inhaler and the refill unit comprises a pressurized aerosol container.

11. A refillable medical device as claimed in claim 10, wherein the inhaler is breath-actuated.

12. A refillable medical device as claimed in claim 1 in the form of a needleless injector.

13. A refillable medical device as claimed in claim 1 in the form of an intra-venous drip system.

* * * * *

UNITED STATES PATENT AND TRADEMARK OFFICE
CERTIFICATE OF CORRECTION

PATENT NO. : 7,080,642 B2
APPLICATION NO. : 10/169034
DATED : July 25, 2006
INVENTOR(S) : Peter D. Hodson It is certified that error appears in the above-identified patent and that said Letters Patent is hereby corrected as shown below:

Title Page, Column 2 (U.S. Patent Documents):
Line 2, After "5,192,548 A" delete "*".

Title Page, Column 2 (U.S. Patent Documents):
Line 4, After 5,899,880 A" delete "*".

Title Page, Column 2 (Foreign Patent Documents):
Line 1, After "2263673" delete "*".

Title Page, Column 2 (Foreign Patent Documents):
Line 2, After "90/13327" delete "*".

Title Page, Column 2 (Foreign Patent Documents):
Line 3, After "90/13328" delete "*".

Title Page, Column 2 (Foreign Patent Documents):
Line 4, After "92/08509" delete "*".

Title Page, Column 2 (Foreign Patent Documents):
Line 5, After "92/17231" delete "*".

Title Page, Column 2 #57 (Abstract):
Line 6, Delete "intravenous" and insert -- intra-venous --, therefor.

Title Page, Column 2:
Line 39 Delete "intravenous" and insert -- intra-venous --, therefor.

Column 3:
Line 23, Delete "intravenous" and insert -- intra-venous --, therefor.

Column 5:
Line 16, After "in" delete "is".

UNITED STATES PATENT AND TRADEMARK OFFICE
CERTIFICATE OF CORRECTION

PATENT NO.         : 7,080,642 B2
APPLICATION NO.    : 10/169034
DATED              : July 25, 2006
INVENTOR(S)        : Peter D. Hodson It is certified that error appears in the above-identified patent and that said Letters Patent is hereby corrected as shown below:

<u>Column 8:</u>
Line 2 Delete "intravenous" and insert -- intra-venous --, therefor Signed and Sealed this First Day of May, 2007

JON W. DUDAS
*Director of the United States Patent and Trademark Office*